(12) United States Patent
Vicario

(10) Patent No.: US 11,883,593 B2
(45) Date of Patent: Jan. 30, 2024

(54) DETERMINING RESPIRATORY MECHANIC PARAMETERS IN THE PRESENCE OF INTRINSIC POSITIVE END-EXPIRATORY PRESSURE

(71) Applicant: KONINKLIJKE PHILIPS N.V., Eindhoven (NL)

(72) Inventor: Francesco Vicario, Boston, MA (US)

(73) Assignee: Koninklijke Philips N.V., Eindhoven (NL)

( * ) Notice: Subject to any disclaimer, the term of this patent is extended or adjusted under 35 U.S.C. 154(b) by 1058 days.

(21) Appl. No.: 16/471,135

(22) PCT Filed: Dec. 20, 2017

(86) PCT No.: PCT/EP2017/083812
§ 371 (c)(1),
(2) Date: Jun. 19, 2019

(87) PCT Pub. No.: WO2018/115119
PCT Pub. Date: Jun. 28, 2018

(65) Prior Publication Data
US 2020/0038610 A1 Feb. 6, 2020

Related U.S. Application Data

(60) Provisional application No. 62/436,552, filed on Dec. 20, 2016.

(51) Int. Cl.
*A61M 16/00* (2006.01)
*A61B 5/08* (2006.01)

(52) U.S. Cl.
CPC ............. *A61M 16/024* (2017.08); *A61B 5/08* (2013.01); *A61M 2016/0027* (2013.01);
(Continued)

(58) Field of Classification Search
CPC .............. A61M 16/021; A61M 16/022; A61M 16/024; A61M 16/026; A61M 16/0003;
(Continued)

(56) References Cited

U.S. PATENT DOCUMENTS

2005/0284476 A1* 12/2005 Blanch ................. A61M 16/00
128/204.23
2007/0062533 A1* 3/2007 Choncholas ........ A61M 16/024
128/204.23
(Continued)

FOREIGN PATENT DOCUMENTS

| WO | 2011/090716 | 7/2011 |
|---|---|---|
| WO | 2016/128846 | 8/2016 |
| WO | 2017/055959 | 4/2017 |

OTHER PUBLICATIONS

International Search Report and Written Opinion dated Mar. 21, 2018 for International Application No. PCT/EP2017/083812 filed Dec. 20, 2017.
(Continued)

*Primary Examiner* — Joseph D. Boecker
*Assistant Examiner* — Brian T Khong
(74) *Attorney, Agent, or Firm* — Daniel H. Brean; Andrew M. Gabriel

(57) ABSTRACT

A system for determining a parameter of respiratory mechanics in the presence of an intrinsic positive end-expiratory pressure during a ventilator support of a patient is provided. The system includes a computer system that comprises one or more in physical processors programmed with computer program instructions which, when executed cause the computer system to: determine breath segmentation data from airway flow information of the patient and airway pressure information of the patient; and determine the parameter of respiratory mechanics in the presence of the intrinsic positive end-expiratory pressure using the deter-
(Continued)

mined breath segmentation data. The parameter of respiratory mechanics includes one or more of the following: respiratory resistance, respiratory elastance, respiratory compliance, the intrinsic positive end-expiratory pressure, a pressure inside the alveoli, and an equivalent pressure generated by the respiratory muscles of the patient.

20 Claims, 3 Drawing Sheets

(52) U.S. Cl.
CPC ............... *A61M 2016/0036* (2013.01); *A61M 2230/005* (2013.01); *A61M 2230/46* (2013.01)

(58) Field of Classification Search
CPC .......... A61M 16/0066; A61M 16/0069; A61M 2016/0027; A61M 2016/003; A61M 2016/0033; A61M 2016/0036; A61M 2016/0039; A61M 2016/0042; A61M 2230/005; A61M 2230/40; A61M 2230/42; A61M 2230/46; A61B 5/08; A61B 5/0803; A61B 5/0806; A61B 5/0809
See application file for complete search history.

(56) References Cited

U.S. PATENT DOCUMENTS

| | | | |
|---|---|---|---|
| 2011/0196251 A1* | 8/2011 | Jourdain | A61M 16/0069 128/204.21 |
| 2012/0000468 A1 | 1/2012 | Milne | |
| 2012/0000470 A1* | 1/2012 | Milne | G16H 50/20 715/781 |
| 2012/0037159 A1* | 2/2012 | Mulqueeny | A61M 16/06 128/204.23 |
| 2014/0171817 A1* | 6/2014 | Blanch | A61M 16/0051 128/204.23 |

OTHER PUBLICATIONS

Vicario et al: "Noninvasive estimation of alveolar pressure", 2016 38th Annual International Conference of the IEEE Engineering in Medicine and Biology Society (EMBC), IEEE, Aug. 16, 2016, pp. 2721-2724.

Mayaud et al: "An open-source software for automatic calculation of respiratoryparameters based on esophageal pressure" Respiratory Physiology & Neurobiology 192 (2014) 1-6.

* cited by examiner

|  | Parameter | Breath 1 | Breath 2 | Breath 3 |
|---|---|---|---|---|
| TRUE | R | 20 | 20 | 20 |
|  | E | 20 | 20 | 20 |
|  | PEEPi | 0 | 3.23 | 3.31 |
| ESTIMATES TAKING INTO ACCOUNT PEEPi | R | 20 | 20 | 20 |
|  | E | 20 | 20 | 20 |
|  | PEEPi | 0 | 3.23 | 3.31 |
| ESTIMATES NOT TAKING INTO ACCOUNT PEEPi | R | 20 | 14.95 | 14.76 |
|  | E | 20 | 27.77 | 28.17 |
|  | PEEPi | 0 | 2.42 | 2.44 |

… # DETERMINING RESPIRATORY MECHANIC PARAMETERS IN THE PRESENCE OF INTRINSIC POSITIVE END-EXPIRATORY PRESSURE

CROSS-REFERENCE TO RELATED APPLICATIONS

This patent application claims the priority benefit under 35 U.S.C. § 371 of international patent application no. PCT/EP2017/083812, filed Dec. 20, 2017, which claims the priority benefit under 35 U.S.C. § 119(e) of U.S. Provisional Application No. 62/436,552 filed on Dec. 20, 2016, the contents of which are herein incorporated by reference.

BACKGROUND OF THE INVENTION

1. Field of the Invention

The present disclosure pertains to a method and a system for delivering a respiratory therapy to a patient and, more particularly, determining parameter(s) of respiratory mechanics in the presence of intrinsic positive end-expiratory pressure (i.e., intrinsic PEEP, $PEEP_i$) in the interaction between such a system and the patient.

2. Description of the Related Art

A ventilation system or ventilator delivers respiratory therapy to a patient by delivering a gas to the patient's pulmonary system at a level above ambient pressure during inspiration.

The need for estimation of the respiratory mechanics of a patient under mechanical ventilation is known in the medical community. Generally, a quantitative assessment of the respiratory mechanics can aid the clinician to: 1) diagnose the disease underlying respiratory failure; 2) monitor the status and progression of the disease; 3) measure the effects of treatments; and 4) tune the ventilator settings to the patient specific needs, and thus minimize the risk of ventilator-induced complications, such as ventilator-induced lung injury (VILI).

Respiratory mechanics is typically described using the first-order linear model as shown in FIG. 1. The equation of motion of the air in the respiratory system in FIG. 1 is shown in Equation 1 below.

$$P_{ao}(t)=RQ(t)+EV(t)+P_{mus}(t)+P_0 \qquad (1)$$

where $P_{ao}(t)$ is the airway opening pressure (measured, for instance, at a Y-piece of the ventilator or estimated by appropriate techniques), Q(t) is the flow of air into and out of the patient respiratory system (measured again at the airway opening or estimated by appropriate techniques), V(t) is the net volume of air delivered by the ventilator to the patient (measured by integrating the airflow signal over time), R is the respiratory resistance, E is the respiratory elastance, $P_0$ is a constant term to account for the pressure at the end of expiration, and $P_{mus}(t)$ is an equivalent pressure representing the force exerted over the breath by the respiratory muscles.

(1/E) is often indicated as compliance, C. Typically $P_0$=PEEP, where PEEP is the positive end-expiratory pressure set in the ventilator. $P_0$ is also a constant term balancing the pressure at the airway opening. $P_{ao}(t)$ is also the pressure at the entrance of the resistive pathway.

Estimating the respiratory mechanics of a patient under mechanical ventilation means estimating the first-order linear model (or other model) representative of the specific patient under treatment. In practice, it requires the estimation of R, E and $P_0$. The measurements of $P_{ao}(t)$, Q(t) and V(t) are typically available. Once R, E and $P_0$ are known, other variables and parameters of interest can be calculated.

For instance, from Equation (1), $P_{mus}(t)$ may be computed. From $P_{mus}(t)$ the clinical parameter often used to characterize the patient effort (WOB, work of breathing) can be computed, too, as the integral over the inhalation time of the product between $P_{mus}(t)$ and Q(t). Furthermore, the pressure inside the alveoli can be computed using Equation (2) below.

$$P_{alv}(t)=P_{ao}(t)-RQ(t) \qquad (2)$$

where $P_{alv}(t)$ is alveolar pressure or pressure inside alveoli (elastic compartment).

Similar to Equation (1), Equation (2) comes from the first-order linear model in FIG. 1. Assessment of $P_{alv}(t)$, in particular of the maximum value it takes during a breath, is very important to avoid barotrauma (i.e., to ensure $P_{alv}(t)$ does not reach values so high that lung tissue might be damaged).

Additionally, the pressure inside the alveoli at the beginning of the breath is useful to assess intrinsic PEEP, $PEEP_i$ or hyperinflation, which are typical phenomena observed in COPD (Chronic Obstructive Pulmonary Disease) patients and have to be eliminated by appropriate changes of ventilator settings. Intrinsic PEEP, $PEEP_i$ and hyperinflation are due to the beginning of a new breath before the previous breath is completely over. This leads to air trapped in the alveoli (i.e., the new breath begins when air from the previous breath has not been completely exhaled). The difference between the pressure inside the alveoli at the onset of a new breath and the pressure at the mouth of the patient delivered by the ventilator at the end of the expiratory phase of the previous breath is known as intrinsic PEEP, $PEEP_i$ or auto-PEEP.

Correct estimation of the respiratory mechanics in COPD patients is important for two main reasons. One, respiratory failure is the leading cause of death from COPD. Second, COPD patients require ventilation at high pressure (high $P_{ao}$), therefore making it necessary to monitor (by non-invasive estimation) their $P_{alv}$ in order to avoid barotrauma.

Intrinsic PEEP, $PEEP_i$ is a valuable piece of information for clinicians. However, it is difficult to assess for several reasons. For example, R in Equation (2) is unknown, therefore estimation of R is required to estimate the intrinsic PEEP, $PEEP_i$. Unfortunately, the estimation of R is extremely difficult in the presence of (unknown) patient effort, $P_{mus}(t)$. Additionally, the estimation of R as well as the respiratory system elastance, E is even more challenging in the presence of the intrinsic PEEP, $PEEP_i$.

Because $P_{mus}(t)$ is not measured, estimating R, E and $P_0$ in Equation (1) via the ordinary Least Square method leads to bias in the estimates. This is due to the fact that the unknown $P_{mus}(t)$ ends up being treated as noise but it is not zero-mean and uncorrelated as the Least Square method requires to yield unbiased estimates. Methods to neutralize the detrimental effect of $P_{mus}(t)$ have been proposed. However, these methods are computationally intensive.

The presence of intrinsic PEEP, $PEEP_i$ itself can create bias in estimates of R and E. Breaths are usually segmented (for breath-by-breath estimation) using the ascending zero-crossing of Q(t) (flow signal). However, in the presence of intrinsic PEEP, $PEEP_i$, before being able to generate positive airflow into the lungs, the patient has first to balance and overcome the pressure trapped in the lungs, i.e., Q(t) crosses zero only when $-P_{mus}(t) > PEEP_i$. This leads to $P_{mus}(t)$ being non-zero (and unknown) at the beginning of the breath, which is a data point often used for the estimation of R and E under the assumption that $P_{mus}=0$. Having non-zero $P_{mus}$ at the beginning of the breath in the presence of $PEEP_i$ causes bias in the estimates of R and E.

A common misconception in the estimation of $PEEP_i$ is that it can be estimated directly from the value of $P_{ao}$ at the ascending zero-crossing of the flow. Indeed, from Equation (2), when Q=0, then $P_{alv}=P_{ao}$. However, the so obtained estimate is an estimate of $P_{alv}$ at the only point (flow zero-crossing) at which $P_{ao}$ corresponds to $P_{alv}$. Unfortunately, that is not $PEEP_i$, since $PEEP_i$ is defined as the alveolar pressure at the onset of the breath. The presence of $PEEP_i$ itself indeed causes the flow to reach 0 after the patient's respiratory effort or ventilator's support started. The flow is still negative when a new breath starts in the presence of $PEEP_i$. In such conditions, the flow zero-crossing occurs after the breath began, therefore the value of $P_{alv}$ obtained from Equation (2) with Q=0 does not correspond to $PEEP_i$.

Therefore, an improved system and method is provided to overcome the above-discussed problems and disadvantages.

SUMMARY OF THE INVENTION

Accordingly, it is an object of one or more embodiments of the present patent application to provide a system for determining a parameter of respiratory mechanics in the presence of an intrinsic positive end-expiratory pressure during a ventilator support of a patient by a ventilator. The system comprises a computer system that comprises one or more physical processors programmed with computer program instructions which, when executed cause the computer system to: determine breath segmentation data from airway flow information of the patient and airway pressure information of the patient; determine the parameter of respiratory mechanics in the presence of the intrinsic positive end-expiratory pressure using the determined breath segmentation data; and provide input to the ventilator based on the determined parameter of respiratory mechanics, the provided input causing an adjustment of one or more settings of the ventilator. The airway flow information and the airway pressure information of the patient are obtained from one or more sensors. The breath segmentation data comprises breath segment airway flow information and breath segment airway pressure information and the breath segmentation data is based on a respiratory effort of the patient. The parameter of respiratory mechanics includes one or more of the following: respiratory resistance, respiratory elastance, respiratory compliance, the intrinsic positive end-expiratory pressure, a pressure inside the alveoli, and an equivalent pressure generated by the respiratory muscles of the patient.

It is yet another aspect of one or more embodiments of the present patent application to provide a method for determining a parameter of respiratory mechanics in the presence of an intrinsic positive end-expiratory pressure during a ventilator support of a patient by a ventilator. The method is implemented by a computer system that comprises one or more physical processors executing computer program instructions which, when executed, perform the method. The method comprises obtaining, from one or more sensors, airway pressure information of the patient and airway flow information of the patient; determining, by the computer system, breath segmentation data from the airway flow information of the patient and the airway pressure information of the patient; determining, by the computer system, the parameter of respiratory mechanics in the presence of the intrinsic positive end-expiratory pressure using the determined breath segmentation data; and providing, by the computer system, input to the ventilator based on the determined parameter of respiratory mechanics, the provided input causing an adjustment of one or more settings of the ventilator. The breath segmentation data comprises breath segment airway flow information and breath segment airway pressure information and the breath segmentation data is based on a respiratory effort of the patient. The parameter of respiratory mechanics includes one or more of the following: respiratory resistance, respiratory elastance, respiratory compliance, the intrinsic positive end-expiratory pressure, a pressure inside the alveoli, and an equivalent pressure generated by the respiratory muscles of the patient.

It is yet another aspect of one or more embodiments to provide a ventilator system for determining a parameter of respiratory mechanics in the presence of an intrinsic positive end-expiratory pressure during a ventilator support of a patient. The system comprises a ventilator configured to deliver breathing gas to the patient; one or more sensors configured to be operatively connected to the ventilator system and determine airway flow information and airway pressure information indicative of flow and pressure, respectively of the breathing gas delivered to the patient; and a computer system that comprises one or more physical processors programmed with computer program instructions which, when executed cause the computer system to: determine breath segmentation data from the airway flow information of the patient and the airway pressure information of the patient, the breath segmentation data comprising breath segment airway flow information and breath segment airway pressure information and the breath segmentation data is based on a respiratory effort of the patient; determine the parameter of respiratory mechanics in the presence of the intrinsic positive end-expiratory pressure using the determined breath segmentation data, the parameter of respiratory mechanics including one or more of the following: respiratory resistance, respiratory elastance, respiratory compliance, the intrinsic positive end-expiratory pressure, a pressure inside the alveoli, and an equivalent pressure generated by the respiratory muscles of the patient; and provide input to the ventilator based on the determined parameter of respiratory mechanics, the provided input causing an adjustment of one or more settings of the ventilator.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

Figure 1:
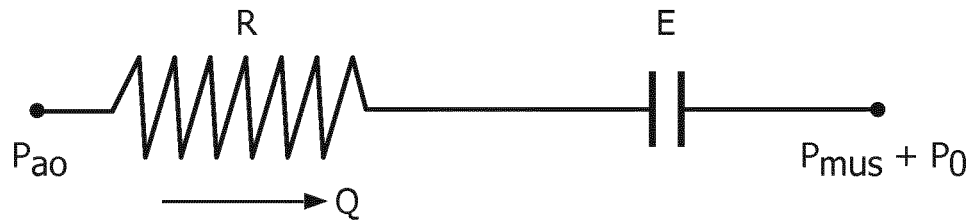
FIG. 1 is a first-order linear model of respiratory mechanics.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present patent application provides a system 100 for determining parameter(s) of respiratory mechanics in the presence of an intrinsic positive end-expiratory pressure during a ventilator support of a patient. As will be clear from the discussions below, in some embodiments, system 100 includes a computer system 102 that has one or more physical processors programmed with computer program instructions which, when executed cause computer system 102 to determine breath segmentation data from airway flow information of the patient and airway pressure information of the patient; and determine the parameter of respiratory mechanics in the presence of the intrinsic positive end-expiratory pressure using the determined breath segmentation data. The parameter of respiratory mechanics includes one or more of the following: respiratory resistance, respiratory elastance, respiratory compliance, the intrinsic positive end-expiratory pressure, a pressure inside the alveoli, and an equivalent pressure generated by the respiratory muscles of the patient. The airway flow information and the airway pressure information of the patient are obtained from one or more sensors (106a . . . 106n). The breath segmentation data comprises breath segment airway flow information and breath segment airway pressure information and the breath segmentation data is based on a respiratory effort of the patient.

The Positive end-expiratory pressure (PEEP) is the pressure in the lungs (e.g., alveolar pressure) above atmospheric pressure (the pressure outside of the body) that exists at the end of expiration. The intrinsic positive end-expiratory pressure (PEEP$_i$) is a Positive end-expiratory pressure caused by an incomplete exhalation. Intrinsic positive end-expiratory pressure, intrinsic PEEP, PEEPi and auto-PEEP, referred to in this application, are exactly the same.

The present patent application provides a correct estimation of the patient's respiratory mechanics in the presence of the intrinsic PEEP, PEEP$_i$ while overcoming the biases (errors) discussed above. The present patent application discloses how to segment the breath for the purpose of estimating the patient's respiratory mechanics as well as how to appropriately correct the estimation formulae to avoid the bias caused by intrinsic PEEP, PEEP$_i$. The idea to get around the presence of intrinsic PEEP, PEEP$_i$ for the estimation of respiratory mechanics is to recognize that that intrinsic PEEP, PEEP$_i$ is defined via the pressure in the alveoli at the onset of the patient's respiratory effort (or the start of ventilator support in the case of mandatory breaths (i.e., breaths that are not triggered by the patient)). After realizing that, appropriate corrections to the formulae used to estimate R and E also need to be made. The necessary corrections are disclosed in this present patent application using an estimation method based on preliminary estimation of the respiratory time constant ($\sigma$) (e.g., as shown in Equation 12 below) and then the estimation of R and E (e.g., as shown in Equations 15c and 16 below).

Figure 2:
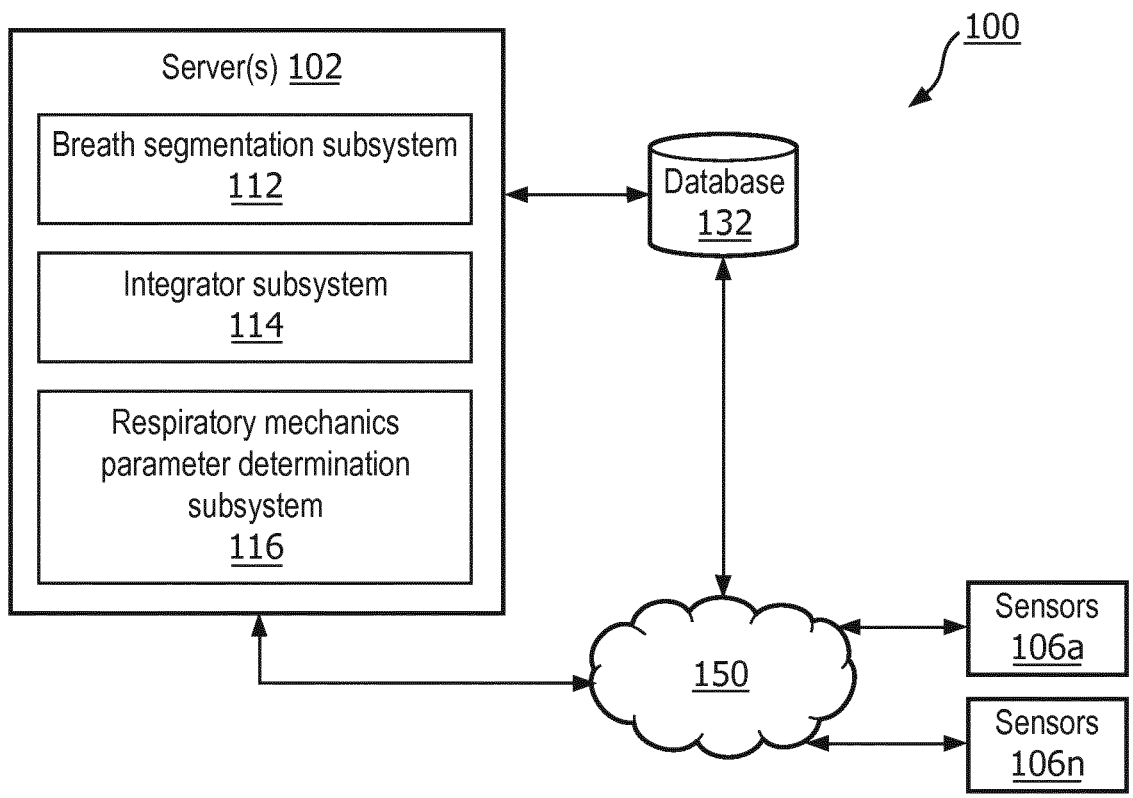
FIG. 2 illustrates an exemplary block diagram of a system for determining parameter(s) of respiratory mechanics in the presence of an intrinsic positive end-expiratory pressure in accordance with an embodiment of the present patent application.
Figure 3:
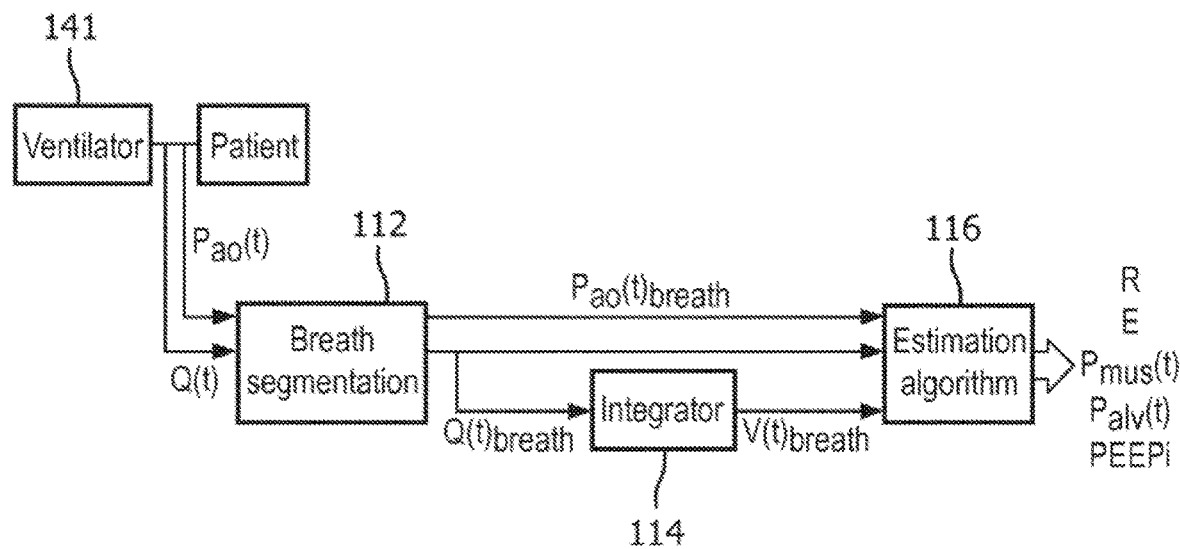
FIG. 3 illustrates another exemplary system for determining parameter(s) of respiratory mechanics in the presence of an intrinsic positive end-expiratory pressure in accordance with an embodiment of the present patent application.

FIGS. 2 and 3 show system 100 for determining the parameter of respiratory mechanics in the presence of the intrinsic PEEP, PEEP$_i$ during the ventilator support of a patient, in accordance with one or more embodiments. As shown in FIG. 2, system 100 may comprise server 102 (or multiple servers 102). Server 102 may comprise breath segmentation subsystem 112, Integrator subsystem 114, respiratory mechanics parameter determination subsystem 116 or other components or subsystems.

In some embodiments, breath segmentation subsystem 112 is configured to take in as an input the waveforms of airflow and pressure measured as close as possible to the mouth of the patient. If proximal sensors are not available, pressure and flow can also be measured at the ventilator outlet. In the case of non-invasive ventilation, the flow that goes as an input to the breath segmentation subsystem 112 may be compensated for leaks.

In some embodiments, breath segmentation subsystem 112 may obtain information associated with patient's airways. In some embodiments, the information may include airway flow information, airway pressure information, or any other airway related information. In some embodiments, the airway flow information of the patient may include information about flow at the airway opening of the patient (e.g., information specifying resistance to airflow at the airway opening during inspiration or expiration, information specifying flow rate at the airway opening during inspiration or expiration, or other information). In some embodiments, the airway pressure information of the patient may include information about pressure at the airway opening of the patient (e.g., information specifying airway pressure at the airway opening during inspiration or expiration or other information). In some embodiments, the airway pressure information of the patient may include information about esophageal pressure (e.g., information specifying airway pressure in the esophagus during inspiration or expiration or other information).

In some embodiments, as shown in FIG. 3, breath segmentation subsystem 112 receives or obtains information about flow of air (into and out of the respiratory system) Q(t) and information about the airway opening pressure (measured, for instance, at a Y-piece of the ventilator) $P_{ao}(t)$ as the inputs.

As another example, the information may be obtained from one or more monitoring devices (e.g., airway flow monitoring device, airway pressure monitoring device, or other monitoring devices). In some embodiments, one or more monitoring devices and associated sensors 106a . . . 106n may be configured to monitor flow at the airway opening. In some embodiments, one or more monitoring devices and associated sensors 106a . . . 106n may be configured to monitor pressure at the airway opening. These monitoring devices may include one or more sensors (106a . . . 106n), such as pressure sensors, pressure transducers, flow rate sensors, or other sensors. Sensors (106a . . . 106n) may, for instance, be configured to obtain information of the patient (e.g., airway pressure, airway flow, or any other airway parameters) or other information related to the patient's airways.

In one scenario, a monitoring device may obtain information (e.g., based on information from one or more sensors (106a . . . 106n)), and provide information to a computer system (e.g., comprising server 102) over a network (e.g., network 150) for processing. In another scenario, upon obtaining the information, the monitoring device may process the obtained information, and provide processed information to the computer system over a network (e.g., network 150). In yet another scenario, the monitoring device may automatically provide information (e.g., obtained or processed) to the computer system (e.g., comprising server 102).

In some embodiments, the sensors may be placed close to the mouth of the patient and/or at the ventilator outlet or other locations, with appropriate compensation algorithms to estimate the corresponding airflow and airway pressure in proximity of the patient's mouth.

As shown in FIG. 3, system 100 also include a ventilator 141 capable of delivering bi-level pressure support. In some embodiment, the ventilator generally includes a pressure generator system configured to provide breathing gas to the patient; a patient or delivery circuit operatively coupled to the pressure generator system to deliver the flow of breathing gas to the patient; and an interface device operatively coupled to the patient circuit to communicate the flow of breathing gas to the airway of the patient.

In some embodiments, pressure generator may be configured to provide a pressurized flow of breathable gas for delivery to the airway of the patient, e.g., via an output of pressure generator, and/or via the patient or delivery circuit. In some embodiments, pressure generator may be configured to adjust one or more of pressure levels, flow, humidity, velocity, acceleration, and/or other parameters of the pressurized flow of breathable gas, e.g., in substantial synchronization with the breathing cycle of the patient.

In some embodiments, a pressurized flow of breathable gas is delivered from the pressure generator to the airway of the patient via the patient or delivery circuit. The delivery circuit may include a conduit and/or the patient interface device. The delivery circuit may sometimes be referred to as the patient interface. The conduit may include a flexible length of hose, or other conduit, either in single-limb or dual-limb configuration that places the patient interface device in fluid communication with the pressure generator. The conduit forms a flow path through which the pressurized flow of breathable gas is communicated between the patient interface device and the pressure generator.

In some embodiments, the patient interface device may be configured to deliver the pressurized flow of breathable gas to the airway of the patient. As such, the patient interface device may include any appliance suitable for this function. In some embodiments, the pressure generator is a dedicated ventilation device and the patient interface device is configured to be removably coupled with another interface device being used to deliver respiratory therapy to the patient. For example, the patient interface device may be configured to engage with and/or be inserted into an endotracheal tube, a tracheotomy portal, and/or other interface appliances. In some embodiments, the patient interface device may be configured to engage the airway of the patient without an intervening device. In this embodiment, the patient interface device may include one or more of an endotracheal tube, a nasal cannula, a tracheotomy tube, a nasal mask, a nasal/oral mask, a full-face mask, a total facemask, and/or other interface devices that communicate a flow of gas with an airway of a subject. The present patent application is not limited to these examples, and contemplates delivery of the pressurized flow of breathable gas to the patient using any subject interface.

Figure 4:
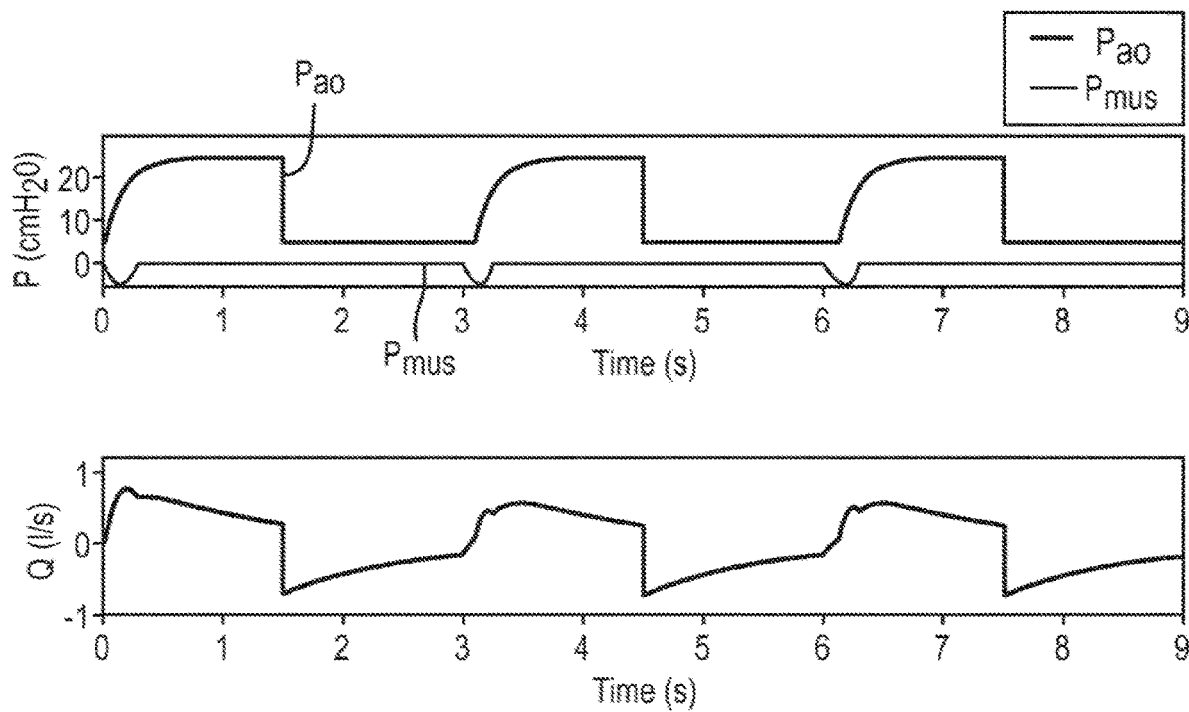
FIG. 4 shows a graphical illustration of pressure and airflow waveforms for a plurality of breath segments in accordance with an embodiment of the present patent application.

In some embodiments, breath segmentation subsystem 112 is configured to segment the breath so that t=0 is defined as the onset of the respiratory effort (i.e., the last time sample at which $P_{mus}$ is zero (negligible)). The breath segmentation data includes breath segment airway flow information and breath segment airway pressure information. Airway flow and airway pressure are measured continuously, they are waveforms. These airway pressure and airway flow waveforms are segmented to extract or isolate one breath at a time. One segment (i.e., one breath) is processed at a time to obtain at every breath an estimate of each parameter of interest. For example, FIG. 4 shows pressure and airflow information for three breath segments—breath segment 1 (from 0 to 3 seconds), breath segment 2 (from 4 to 6 seconds) and breath segment 3 (from 6 to 9 seconds).

Breath segmentation subsystem 112 is configured to segment the breath based on the respiratory effort (i.e., instead of flow ascending zero-crossings). The first sample of the breath (t=0) is the last time sample before the respiratory muscles start exerting force (pressure), which implies that $P_{mus}(0)=0$.

In some embodiments, breath segmentation subsystem 112 is configured to segment the breath based on a predetermined breath segmentation criterion. In some embodiments, the predetermined breath segmentation criterion is based on the respiratory effort of the patient. In some embodiments, the predetermined breath segmentation criterion includes the beginning of the breath and the end of the breath.

In some embodiments, the estimation of respiratory mechanics does not have to be real-time in a strict sense but may be pseudo-real-time (e.g., estimates for a breath can be given at the end of that breath or during the next breath). Therefore, detection of t=0 as defined above to segment breath data for the purpose of parameter estimation can be done off-line as opposed, for instance, to its detection for the purpose of triggering. The typical triggering delay is compensated off-line (i.e., once the data for the breath under investigation have been collected). The problem of detecting the start of patient's effort for breath segmentation is therefore simpler than for triggering. As shown in the example in FIG. 4, the onset of the respiratory effort in pressure control ventilation can be detected as an increase in the slope of the airflow waveform.

At t=0, in some embodiments, the volume is reset, i.e., $V(0)=0$. At t=0, $P_{mus}(0)=0$. At t=0, Equation (1) may be rewritten as shown in Equation (3a) below.

$$P_{ao}(0)=RQ(0)+EV(0)+P_{mus}(0)+P_0 \quad (3a)$$

where $P_{ao}(0)$ is the airway opening pressure measured at t=0, $Q(0)$ is the flow of air into and out of the patient respiratory system measured at t=0, $V(0)$ is the net volume of air delivered by the ventilator to the patient measured by integrating $Q(0)$, R is the respiratory resistance, E is the respiratory elastance, $P_0$ is a constant term to account for the pressure at the end of expiration, and $P_{mus}(0)$ is an equivalent pressure representing the force exerted over the breath by the respiratory muscles.

At t=0, as $V(0)=0$ and $P_{mus}(0)=0$, Equation (3a) can then be simplified as shown in Equation (3b) below.

$$P_{ao}(0)=RQ(0)+P_0 \quad (3b)$$

The terms in Equation (3b) can then be rearranged to solve for $P_0$ as shown in Equation (4) below. Equation (4) is an equation defining $P_0$.

$$P_0=P_{ao}(0)-RQ(0) \quad (4)$$

As shown in Equation (2), the difference between $P_{ao}$ and RQ yields, in accordance with the first-order linear model shown in FIG. 1, the alveolar pressure $P_{alv}$. The definition of $P_0$ in Equation (4) indeed corresponds to the more physical interpretation in Equation (5) below.

$$P_0=P_{alv}(0) \quad (5)$$

Positive end-expiratory pressure (PEEP) is defined as $P_{alv}$ at the end of expiration (i.e., right before the new breath is initiated by the patient). This is shown by Equation (6) below.

$$PEEP=P_{alv}(0) \quad (6)$$

Positive end-expiratory pressure, PEEP is determined by two factors: i) extrinsic PEEP, $PEEP_e$ (i.e., the end-expiratory pressure applied by the ventilator (usually known, since it should correspond to the value set in the ventilator or is directly measured by a pressure sensor)); ii) intrinsic PEEP, $PEEP_i$ (i.e., the additional pressure in the alveoli due to air trapped in the lungs because of incomplete exhalation prior to the start of the new breath). In mathematical terms, the Positive end-expiratory pressure, PEEP may be represented in terms of the extrinsic PEEP, $PEEP_e$ and the intrinsic PEEP, $PEEP_i$ as shown in Equation (7) below.

$$PEEP=PEEPe+PEEPi \quad (7)$$

Estimation of PEEP or intrinsic PEEP, $PEEP_i$ may then be brought down to the estimation of $P_0$ with the caveat of using the above definition for t=0 in the segmentation of the respiratory waveforms.

Comparing Equations (4) to (7), the Positive end-expiratory pressure, PEEP, the extrinsic PEEP, $PEEP_e$ and the intrinsic PEEP, $PEEP_i$ may be represented as shown in Equations 8a-8c, respectively.

$$PEEP=P_0 \quad (8a)$$

$$PEEPe=P_0(0) \quad (8b)$$

$$PEEPi=-RQ(0) \quad (8c)$$

Estimating $P_0$ as defined above is then extremely valuable by itself, since it gives access to $PEEP_i$. Another benefit of the above development is that it neutralizes the negative effect that neglecting $PEEP_i$ has on the estimates of respiratory resistance (R) and elastance (E). In the rest of this present patent application, estimation of R, E, and $P_{alv}(t)$ are discussed. Indeed, correct estimates of R and E provide estimates of $P_{alv}$ (via equation (2)) at any time sample.

In some embodiments, integrator subsystem 114, as shown in FIGS. 2 and 3, is configured to receive the breath segment airway flow information, $Q(t)_{breath}$, and to determine breath segment volume (of air delivered by the ventilator to the patient) information, $V(t)_{breath}$.

In some embodiments, respiratory mechanics parameter determination subsystem 116 is configured to receive the breath segment volume information, $V(t)_{breath}$ from integrator subsystem 114, and receive the breath segment airway flow information, $Q(t)_{breath}$ from breath segmentation subsystem 112 and the breath segment pressure information, $P_{ao}(t)_{breath}$ from breath segmentation subsystem 112.

In some embodiments, respiratory mechanics parameter determination subsystem 116 is configured to determine the parameter of respiratory mechanics in the presence of the intrinsic PEEP, $PEEP_i$ using the determined breath segmentation data. The parameter of respiratory mechanics includes one or more of the following: respiratory resistance, respiratory elastance, respiratory compliance, the intrinsic PEEP, $PEEP_i$, a pressure inside the alveoli, and an equivalent pressure generated by the respiratory muscles of the patient.

The mechanical properties of the respiratory system are typically described using two parameters, the respiratory resistance, R and the respiratory elastance, E. The estimation algorithm of respiratory mechanics parameter determination subsystem 116 described below integrates the above developments into a two-step procedure for the estimation of R and E. The first step includes the estimation of the ratio of R and E, also known as respiratory time constant, τ. The second step recovers R and E. Both steps take correctly into account the presence of intrinsic PEEP, $PEEP_i$, whose estimate can also be recovered in the second step, if desired.

During the expiration, $P_{mus}(t)$ can be assumed to be zero. Equation (1) then becomes Equation (9) as shown below.

$$P_{ao}(t)=RQ(t)+EV(t)+P_0 \quad (9)$$

Plugging the definition of $P_0$ derived in Equation (4) into Equation (9), Equation (10a) is obtained. The terms in Equation (10a) are then rearranged to be as shown in Equation (10b).

$$P_{ao}(t)=RQ(t)+EV(t)+P_{ao}(0)-RQ(0) \quad (10a)$$

$$P_{ao}(t)-P_{ao}(0)=R(Q(t)-Q(0))+EV(t) \quad (10b)$$

During the expiration, the ventilator is controlled to provide, after some time from cycling off, a constant positive end-expiratory pressure (PEEP$_e$) until a new breath initiates. Therefore, by definition, P$_{ao}$(t)=P$_{ao}$(0) and Equation (10b) becomes Equation (11) as shown below.

$$0=R(Q(t)-Q(0))+EV(t) \quad (11)$$

The terms in Equation (11) can be solved for the respiratory time constant τ=R/E. The respiratory time constant τ is the ratio of the respiratory resistance, R and the respiratory elastance, E. The definition of the respiratory time constant τ is shown in Equation (12) below.

$$\tau = -\frac{V(t)}{Q(t)-Q(0)} \quad (12)$$

Equation (12) is valid for several time samples during the expiration and an estimate oft can be obtained by the least-squares method or any other technique (e.g., median) as would be appreciated by one skilled in the art.

During the inhalation, P$_{mus}$(t) in Equation (1) cannot generally be ignored. However, the time sample at the end of inhalation (t$_{EOI}$) (i.e., right before the ventilator cycles off) is the most likely at which the respiratory muscles effort is zero. The airway opening pressure, P$_{ao}$ measured at the end of inhalation (t$_{EOI}$) can be written as shown in Equation (13).

$$P_{ao}(t_{EOI})=RQ(t_{EOI})+EV(t_{EOI})+P_0 \quad (13)$$

Plugging the definition of P$_0$ derived in Equation (4) into Equation (13), Equation (14) is obtained.

$$P_{ao}(t_{EOI})-P_{ao}(0)=R(Q(t_{EOI})-Q(0))+EV(t_{EOI}) \quad (14)$$

From the estimate oft in Equation (12), one unknown between R and E in Equation (1) can be eliminated and the other unknown between R and E can be solved.

For instance, replacing R with τE, E can be solved as shown in Equations (15a)-(15c).

$$P_{ao}(t_{EOI}) - P_{ao}(0) = \tau E(Q(t_{EOI}) - Q(0)) + EV(t_{EOI}) \quad (15a)$$

$$P_{ao}(t_{EOI}) - P_{ao}(0) = E(\tau(Q(t_{EOI}) - Q(0)) + V(t_{EOI})) \quad (15b)$$

$$E = \frac{P_{ao}(t_{EOI}) - P_{ao}(0)}{\tau(Q(t_{EOI}) - Q(0)) + V(t_{EOI})} \quad (15c)$$

Once E is known, R can be recovered from the definition of τ as shown in Equation (16).

$$R=\tau E \quad (16)$$

Finally, the intrinsic PEEP, PEEP$_i$ can be estimated, for example, by recovering it directly from Equation (4). The knowledge of R indeed gives access to the estimation of P$_{alv}$(t) over the entire breath as shown in Equation (17).

$$P_{alv}(t)=P_{ao}(t)-RQ(t) \quad (17)$$

Other clinical parameters of interest can be found, for instance, the maximum alveolar pressure. Similarly, relying on the estimates obtained for R and E, P$_{mus}$(t) over the entire breath is estimated as shown in Equation (18).

$$P_{mus}(t)=P_{ao}(t)-RQ(t)-EV(t)-\text{PEEP} \quad (18)$$

where PEEP=P$_{alv}$(0) as shown in Equation (6).

Thus, respiratory mechanics parameter determination subsystem 116 is first configured to estimate of the respiratory time constant τ (=R/E), for example, using the Equation (12). This estimate is valid for all the time samples during exhalation at which the ventilator is providing the set PEEP.

Different estimators may serve the purpose (least-squares, median, etc.). It is advisable to use data between the sample at which the maximum expiratory flow occurs and the sample at which the flow becomes negligible.

Respiratory mechanics parameter determination subsystem 116 is then configured to determine one unknown between R and E using the estimate of the respiratory time constant τ. For instance, replacing R with τ E, E can be determined as shown in Equation (15c). Once E is known, R can be recovered from the definition of the respiratory time constant τ=R/E. Relying on the estimates obtained for R and E, PEEP$_i$ is estimated using Equation (8c); Paiv(t) over the entire breath is estimated using Equation (17); and P$_{mus}$(t) over the entire breath is estimated using Equation (18), where PEEP=P$_{alv}$(0).

As shown in FIG. 3, the output of respiratory mechanics parameter determination subsystem 116 is, at every breath, a set of estimates fully characterizing the patient's respiratory mechanics. In some embodiments, the set of estimates fully characterizing the patient's respiratory mechanics may include one or more of the following: respiratory resistance, respiratory elastance, respiratory compliance, the intrinsic PEEP, PEEP$_i$, a pressure inside the alveoli, and an equivalent pressure generated by the respiratory muscles of the patient.

Simulated waveforms for the pressure and the airflow (e.g., as shown in FIG. 4) are used to test the estimation algorithm of respiratory mechanics parameter determination subsystem 116. That is, to show the benefit of taking into account the possible presence of PEEP$_i$, the above algorithm of respiratory mechanics parameter determination subsystem 116 is demonstrated via simulated waveforms for the pressure and the airflow (as shown in FIG. 4) and compared with the same algorithm without taking into account PEEP$_i$.

For example, the waveforms for the pressure and the airflow are simulated numerically from a first-order linear model of the respiratory mechanics as shown in FIG. 1 with R=20 cmH$_2$O·s/L and E=20 cmH$_2$O/L, subject to pressure control ventilation (PEEP=5 cmH$_2$O, P=20 cmH$_2$O) triggered by the patient (P$_{mus}$ non-zero for 0.3 seconds with negative peak at −5 cmH20).

These waveforms for the pressure and the airflow are shown in FIG. 4. For example, the top graph of FIG. 4 shows the pressure waveform. That is, pressure is on the left hand side Y-axis of the graph and is measured in cmH$_2$0. Time is on the X-axis of the graph and is measured in seconds. In the top graph of FIG. 4, the waveforms for P$_{ao}$ (i.e., the airway opening pressure (measured, for instance, at the Y-piece of the ventilator)) and P$_{mus}$ (i.e., an equivalent pressure representing the force exerted over the breath by the respiratory muscles) are both shown.

The bottom graph of FIG. 4 shows the airflow waveform. That is, airflow is on the left hand side Y-axis of the graph and is measured in Liters/second, L/sec or L/s. Time is on the X-axis of the graph and is measured in seconds.

The version of the above estimation algorithm that does not take into account the possible presence of PEEP$_i$ in the estimation of R and E is obtained by setting Q(0)=0 in the estimation formulae to find τ, R, and E. The nominal (true) and estimated values of R, E, and PEEPi are shown in Table of FIG. 5. The first breath does not show intrinsic PEEP, PEEP$_i$ at its start and, as expected, R and E are correctly estimated by either version of the algorithm of respiratory mechanics parameter determination subsystem 116. The second and third breaths exhibit intrinsic PEEP, PEEP$_i$ and demonstrate the benefit of taking into account the possible presence of the intrinsic PEEP, $PEEP_i$ in the estimation algorithm of respiratory mechanics parameter determination subsystem 116.

In some embodiments, the various computers and subsystems illustrated in FIGS. 2 and 3 may comprise one or more computing devices that are programmed to perform the functions described herein. The computing devices may include one or more electronic storages (e.g., database 132, or other electronic storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other communication technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information received from the servers, information received from client computing platforms, or other information that enables the servers to function as described herein.

The processors may be programmed to provide information processing capabilities in the servers. As such, the processors may include one or more of a digital processor, an analog processor, or a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112, 114, 116 or other subsystems. The processors may be programmed to execute computer program instructions by software; hardware; firmware; some combination of software, hardware, or firmware; and/or other mechanisms for configuring processing capabilities on the processors.

It should be appreciated that the description of the functionality provided by the different subsystems 112-116 described herein is for illustrative purposes, and is not intended to be limiting, as any of subsystems 112-116 may provide more or less functionality than is described. For example, one or more of subsystems 112-116 may be eliminated, and some or all of its functionality may be provided by other ones of subsystems 112-116. As another example, additional subsystems may be programmed to perform some or all of the functionality attributed herein to one of subsystems 112-116.

It should be appreciated that the different subsystems 112-116 performing the operations illustrated in FIG. 3 may reside in the ventilator itself. In other embodiments, the different subsystems 112-116 performing the operations illustrated in FIG. 3 may reside in an independent monitoring device.

In some embodiments, user interface may be configured to provide an interface between system and a user (e.g., a patient or a caregiver, etc.) through which the user can provide information to and receive information from system 100. This enables data, results, and/or instructions and any other communicable items, collectively referred to as "information," to be communicated between the user and system 100. Examples of interface devices suitable for inclusion in user interface include a keypad, buttons, switches, a keyboard, knobs, levers, a display screen, a touch screen, speakers, a microphone, an indicator light, an audible alarm, and a printer. Information may be provided to the patient by the user interface in the form of auditory signals, visual signals, tactile signals, and/or other sensory signals. It is to be understood that other communication techniques, either hard-wired or wireless, are also contemplated herein as the user interface. For example, in one embodiment, the user interface may be integrated with a removable storage interface provided by electronic storage 132. In this example, information is loaded into system 100 from removable storage (e.g., a smart card, a flash drive, a removable disk, etc.) that enables the user(s) to customize system 100. Other exemplary input devices and techniques adapted for use with system 100 as user interface include, but are not limited to, an RS-232 port, RF link, an IR link, modem (telephone, cable, Ethernet, internet or other). In short, any technique for communicating information with system 100 is contemplated as the user interface.

Figures 5, 6:
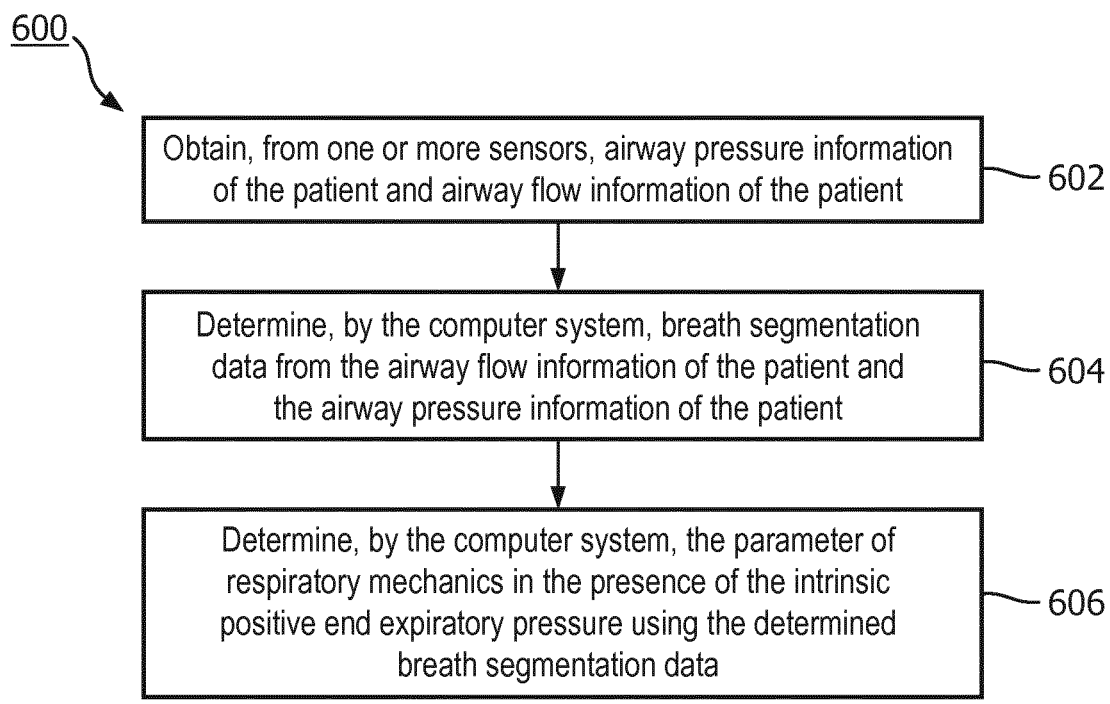
FIG. 5 shows true and estimated values of respiratory resistance, R; respiratory elastance, E, and intrinsic positive end-expiratory pressure for a plurality of breath segments shown in FIG. 4.
FIG. 6 shows a method for determining parameter(s) of respiratory mechanics in the presence of an intrinsic positive end-expiratory pressure in accordance with an embodiment of the present patent application.

FIG. 6 is a flow chart for determining parameter(s) of respiratory mechanics in the presence of intrinsic PEEP, $PEEP_i$ during a ventilator support of a patient. Referring to FIG. 6, a method 600 for determining parameter(s) of respiratory mechanics in the presence of intrinsic PEEP, $PEEP_i$ during a ventilator support of a patient is provided. Method 600 is implemented by computer system 102 that comprises one or more physical processors executing computer program instructions which, when executed, perform method 600. In some embodiments, method (or algorithm) 600 of this present application may be implemented in the hardware (processor/memory) of the ventilator itself. In some embodiments, method (or algorithm) 600 of this present application may be implemented in the external hardware, computer, server, cloud, etc.

Method 600 comprises: obtaining, from one or more sensors (106a . . . 106n), airway pressure information of the patient and airway flow information of the patient at procedure 602; determining, by computer system 102, breath segmentation data from the airway flow information of the patient and the airway pressure information of the patient at procedure 604; and determining, by computer system 102, the parameter of respiratory mechanics in the presence of the intrinsic PEEP, $PEEP_i$ using the determined breath segmentation data at procedure 606. The breath segmentation data comprises breath segment airway flow information and breath segment airway pressure information and the breath segmentation data is based on a respiratory effort of the patient. The parameter of respiratory mechanics includes one or more of the following: respiratory resistance, respiratory elastance, respiratory compliance, the intrinsic PEEP, $PEEP_i$, a pressure inside the alveoli, and an equivalent pressure generated by the respiratory muscles of the patient.

The present patent application provides a ventilator or respiratory monitoring device that provides intrinsic PEEP, $PEEP_i$ estimation in assisted and supported modes of ventilation. The system of the present patent application can be used in both invasive and non-invasive ventilation. Any type of patient can benefit from the system of the present patent application, but patients showing intrinsic PEEP, $PEEP_i$ (e.g., COPD patients) benefits the most due to the lack of respiratory mechanics estimation algorithms effective in the presence of intrinsic PEEP, $PEEP_i$.

The system of the present patent application provides the real-time non-invasive estimate of R, E (or C), $P_{mus}(t)$, $P_{alv}(t)$ and $PEEP_i$ offering a complete characterization of the respiratory mechanics of the specific patient under ventilation support modalities. Such estimates can be applied to 1) detect changes in the health conditions (e.g., stiffening of the lungs, obstruction in the airways, recovering from anesthesia) of the patient, 2) compute the effort per breath made by the patient, 3) trigger the ventilator, 4) automatically adjust pressure support levels so as to keep the patient in "safe zone" avoiding respiratory muscle atrophy and fatigue, 5) personalize physiological models to a specific patient, for prediction and therapeutic path optimization, and 6) patients suffering from COPD, whose characteristic intrinsic PEEP, $PEEP_i$ typically prevents one from having unbiased estimates of the respiratory mechanics. The system of the present patent application is applicable to both invasive and non-invasive ventilation.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. A system comprising:
    one or more physical processors programmed with computer program instructions which, when executed, cause the system to:
        determine breath segmentation data indicating a first time associated with an onset of respiratory effort and a second time associated with an end of inhalation of a breathing patient receiving support from a ventilator;
        use: (a) a difference in airway flow values sampled at the first time and during exhalation; and (b) airway volume values sampled during the exhalation determine a respiratory time constant value;
        use the respiratory time constant value in combination with airway pressure values and the airway flow values sampled at the first time and the second time, and an airway volume value sampled at the second time, to thereafter recover one or more of respiratory resistance and respiratory elastance; and
        provide, using the one or more of the respiratory resistance and respiratory elastance, a parameter of respiratory mechanics in a presence of an intrinsic positive end-expiratory pressure ($PEEP_i$) as input to the ventilator, causing an adjustment of one or more settings of the ventilator.

2. The system of claim 1, wherein the first time is a last time for sampling before respiratory muscles of the breathing patient start exerting force.

3. The system of claim 1, wherein the airway pressure values are obtained from a Y-piece of the ventilator.

4. The system of claim 1, wherein the second time is a last time for sampling at the end of inhalation before the ventilator cycles off.

5. The system of claim 1, wherein the respiratory time constant value is determined by: $\tau=-V(t)/Q(t)-Q(0)$;
    wherein:
    $\tau$ is the respiratory time constant value;
    $V(t)$ is the airway volume value delivered by the ventilator during the exhalation;
    $Q(t)$ is the airway flow value during the exhalation; and
    $Q(0)$ is the airway flow value at the first time.

6. The system of claim 1, wherein to recover the one or more of the respiratory resistance and respiratory elastance using the respiratory time constant value comprises:
    determining the respiratory elastance, E, by: $E=P_{ao}(t_{EOI})-P_{ao}(0)/\tau(Q(t_{EOI})-Q(0))+V(t_{EOI})$;
    wherein:
    $P_{ao}(t_{EOI})$ is the airway pressure value at the second time;
    $P_{ao}(0)$ is the airway pressure value at the first time;
    $\tau$ is the respiratory time constant value;
    $Q(t_{EOI})$ is the airway flow value at the second time;
    $Q(0)$ is the airway flow value at the first time; and
    $V(t_{EOI})$ is the airway volume value at the second time.

7. The system of claim 1, wherein the one or more physical processors are programmed with the computer program instructions which, when executed cause the system to determine the $PEEP_i$ by: $PEEPi=-RQ(0)$; and
    wherein:
    R is the resistance; and
    Q is the airway flow information at the first time.

8. A method being implemented by a computer system, the method comprising:
    obtaining, from one or more sensors, airway pressure values of a patient and airway flow values of the patient;
    determining, by the computer system, breath segmentation data indicating a first time associated with an onset of respiratory effort and a second time associated with an end of inhalation of the patient receiving support from a ventilator;

using: (a) a difference in the airway flow values sampled at the first time and during exhalation; and (b) airway volume values sampled during the exhalation determine a respiratory time constant value;

using the respiratory time constant value in combination with airway pressure values and the airway flow values sampled at the first time and the second time, and an airway volume value sampled at the second time, to thereafter recover one or more of respiratory resistance and respiratory elastance; and providing, using the one or more of the respiratory resistance and respiratory elastance, a parameter of respiratory mechanics in a presence of an intrinsic positive end-expiratory pressure (PEEP$_i$)

as input to the ventilator, causing an adjustment of one or more settings of the ventilator.

9. The method of claim 8, wherein the first time is a last time for sampling before respiratory muscles of the patient start exerting force.

10. The method of claim 8, wherein the airway pressure values are obtained from a Y-piece of the ventilator.

11. The method of claim 8, wherein the second time is a last time for sampling at the end of inhalation before the ventilator cycles off.

12. The method of claim 8, wherein the respiratory time constant value is determined by: $\tau = V(t)/Q(t) - Q(0)$;

wherein:
$\tau$ is the respiratory time constant value;
$V(t)$ is the airway volume value delivered by the ventilator during the exhalation;
$Q(t)$ is the airway flow value during the exhalation; and
$Q(0)$ is the airway flow value at the first time.

13. The method of claim 8, wherein to recover one or more of the respiratory resistance and respiratory elastance using the respiratory time constant value comprises:

determining the respiratory elastance, E, by: $E = P_{ao}(t_{EOI}) - P_{ao}(0)/\tau(Q(t_{EOI}) - Q(0)) + V(t_{EOI})$;

wherein:
$P_{ao}(t_{EOI})$ is the airway pressure value at the second time;
$P_{ao}(0)$ is the airway pressure value at the first time;
$\tau$ is the respiratory time constant value;
$Q(t_{EOI})$ is the airway flow value at the second time;
$Q(0)$ is the airway flow value at the first time; and
$V(t_{EOI})$ is the airway volume value at the second time.

14. A ventilator system comprising:
a ventilator configured to deliver breathing gas to a breathing patient;
one or more sensors configured to be operatively connected to the ventilator system and determine airway flow information and airway pressure information indicative of flow and pressure, respectively, of the breathing gas; and
a computer system that comprises one or more physical processors programmed with computer program instructions which, when executed, cause the computer system to:

determine breath segmentation data indicating a first time associated with an onset of respiratory effort and a second time associated with an end of inhalation of the breathing patient;

use: (a) a difference in airway flow values sampled at a first time and during exhalation; and (b) airway volume values sampled during the exhalation determine a respiratory time constant value;

use the respiratory time constant value in combination with airway pressure values and the airway flow values sampled at the first time and the second time, and an airway volume value sampled at the second time, to thereafter recover one or more of respiratory resistance and respiratory elastance; and provide, using the one or more of the respiratory resistance and respiratory elastance, a parameter of respiratory mechanics in a presence of an intrinsic positive end-expiratory pressure (PEEP$_i$)

as input to the ventilator, causing an adjustment of one or more settings of the ventilator.

15. The ventilator system of claim 14, wherein the ventilator includes a pressure generator system configured to provide the breathing gas to the breathing patient; a patent circuit operatively coupled to the pressure generator system to deliver a flow of breathing gas to the breathing patient; and an interface device operatively coupled to the patient circuit to communicate the flow of breathing gas to an airway of the breathing patient.

16. The ventilator system of claim 14, wherein the first time is a last time for sampling before respiratory muscles of the breathing patient start exerting force.

17. The ventilator system of claim 14, wherein the airway pressure values are obtained from a Y-piece of the ventilator.

18. The ventilator system of claim 14, wherein the second time is a last time for sampling at the end of inhalation before the ventilator cycles off.

19. The ventilator system of claim 14, wherein the respiratory time constant value is determined by: $\tau = -V(t)/Q(t) - Q(0)$;

wherein:
$\tau$ is the respiratory time constant value;
$V(t)$ is the airway volume value delivered by the ventilator during the exhalation;
$Q(t)$ is the airway flow value during the exhalation; and
$Q(0)$ is the airway flow value at the first time.

20. The ventilator system of claim 14, wherein to recover the one or more of the respiratory resistance and respiratory elastance using the respiratory time constant value comprises:

determining the respiratory elastance, E, by: $E = P_{ao}(t_{EOI}) - P_{ao}(0)/\tau(Q(t_{EOI}) - Q(0)) + V(t_{EOI})$;

wherein:
$P_{ao}(t_{EOI})$ is the airway pressure value at the second time;
$P_{ao}(0)$ is the airway pressure value at the first time;
$\tau$ is the respiratory time constant value;
$Q(t_{EOI})$ is the airway flow value at the second time;
$Q(0)$ is the airway flow value at the first time; and
$V(t_{EOI})$ is the airway volume value at the second time.

* * * * *